United States Patent
Ruijssenaars et al.

(10) Patent No.: US 9,045,787 B2
(45) Date of Patent: Jun. 2, 2015

(54) POLYPEPTIDES HAVING OXIDOREDUCTASE ACTIVITY AND THEIR USES

(75) Inventors: Harald Johan Ruijssenaars, Driebergen-Rijsenburg (NL); Nick Johannes Petrus Wierckx, Delft (NL); Frank Wouter Koopman, Utrecht (NL); Adrianus Johannes Jozef Straathof, Delft (NL); Johannes Hendrik De Winde, Voorhout (NL)

(73) Assignee: Purac Biochem B.V., Gorinchem (NL)

( * ) Notice: Subject to any disclaimer, the term of this patent is extended or adjusted under 35 U.S.C. 154(b) by 590 days.

(21) Appl. No.: 13/393,496

(22) PCT Filed: Sep. 2, 2010

(86) PCT No.: PCT/EP2010/062896
§ 371 (c)(1),
(2), (4) Date: Aug. 16, 2012

(87) PCT Pub. No.: WO2011/026913
PCT Pub. Date: Mar. 10, 2011

(65) Prior Publication Data
US 2012/0309918 A1    Dec. 6, 2012

(30) Foreign Application Priority Data
Sep. 2, 2009 (EP) .................................. 09169227
Oct. 8, 2009 (EP) .................................. 09172555

(51) Int. Cl.
*C12P 17/04* (2006.01)
*C12N 1/20* (2006.01)
*C12N 9/04* (2006.01)

(52) U.S. Cl.
CPC ............... *C12P 17/04* (2013.01); *C12N 9/0006* (2013.01)

(58) Field of Classification Search
CPC .............................. C12P 17/04; C12N 9/0006
USPC .............................................. 435/252.3, 189
See application file for complete search history.

(56) References Cited

U.S. PATENT DOCUMENTS
2007/0243594 A1    10/2007    Gupta et al.

FOREIGN PATENT DOCUMENTS
WO    2009/023174    2/2009

OTHER PUBLICATIONS

Written opinion for PCT/EP2010/062896 (2010).*
Kroger et al., "A New Approach for the Production of 2,5-Furandicarboxylic Acid by In Situ Oxidation of 5-Hydroxymethylfurfural Starting for Fructose," Topics in Catalysis, vol. 13, pp. 237-242, (2000).
Mitsukura et al., "Oxidation of Heterocyclic and Aromatic Aldehydes to the Corresponding Carboxylic Acids by Acetobacter and Serratia Strains," biotechnology Letters, vol. 26, pp. 1643-1648, (2004).
van Deurzen et al., "Chloroperoxidase-Catalyzed Oxidation of 5-Hydroxymethylfurfural," J. Carbohydrate chemistry, vol. 16, No. 3, pp. 299-309, (1997).
Lucas et al., "Complete Sequence of Chromosome 1 of Burkholderia Phytofirmans PSJN," Database UniProt Accession No. XP002559847, 1 page, (Jul. 1, 2008).
Copeland et al., "Complete Sequence of Plasmid 1 Ofburkholderia Phymatum STM815," Database UniProt Accession No. XP002559848, 1 page, (Jun. 10, 2008).
International Search Report for PCT/EP2010/062896 Mailed Nov. 11, 2010.

* cited by examiner

*Primary Examiner* — Tekchand Saidha
(74) *Attorney, Agent, or Firm* — Bret E. Field; Bozicevic, Field & Francis LLP

(57) ABSTRACT

The invention relates to a polypeptide having oxidoreductase activity which comprises the amino acid sequence set out in SEQ ID NO: 3 or an amino acid sequence encoded by the nucleotide sequence of SEQ ID NO: 4, or a variant polypeptide thereof having 45% or more sequence identity with the sequence of SEQ ID NO: 3. The invention also relates to a process for the production of 2,5-furan-dicarboxylic acid (FDCA) or production of 5-hydroxymethyl-2-furancarboxylic acid (HMF acid).

14 Claims, 11 Drawing Sheets

*Methylobacterium*
　　*radiotolerans* JCM 2831
　　　　　　*Mrad2831_*
　　Sp. 4-46
　　　　　　*M446_*

*nodulans* ORS2060
　　　　　　*Mnod_*

Acidiphilium
　　*cryptum* JF-5
　　　　　　*Acry_*

Dinoroseobacter
　　*shibae* DFL 12　　　　　　52/166　40/170　54/176
　　　　　　*Dshi_*　　　　　　3714　　3715　　3716

POLYPEPTIDES HAVING OXIDOREDUCTASE ACTIVITY AND THEIR USES

CROSS REFERENCE TO RELATED APPLICATIONS

This application is a §371 National Stage Application of PCT/EP2010/062896, filed Sep. 2, 2010, which claims priority to European Application Nos. 09169227.7, filed Sep. 2, 2009; and 09172555.6, filed Oct. 8, 2009.

BACKGROUND OF THE INVENTION

1. Field of the Invention

The invention relates to polypeptide having oxidoreductase activity and to polynucleotide sequences comprising a gene that encodes the polypeptide. The invention further relates to the production of 2,5-Furan-dicarboxylic acid (FDCA). Also included in the invention are cells transformed with a polynucleotide according to the invention suitable for producing these polypeptides, which may also be used for biotransformation of hydroxymethylfurfural (HMF) to FDCA.

2. Description of Related Art 2,5-Furan-dicarboxylic acid (FDCA) has large potential to become a bio-based alternative for terephthalate in the production of polyesters such as PET. As such and for other reasons FDCA was identified as one of the Top-12 priority chemicals in the DOE report on Top Value-Added Chemicals from Biomass (Top Value-Added Chemicals from Biomass, Volume I—Results of screening for potential Candidates from Sugars and Synthesis gas, Department of Energy (USA), 2004). This compound may be obtained by oxidation of 5-hydroxymethylfurfural (HMF), which can be produced by heating hexose sugars under acid conditions. The DOE report discloses on page 27, some potential utilities for FDCA. These include a role as substrate for the production of succinic acid, 2,5-bis(aminomethyl)-tetrahydrofuran, 2,5-dihydroxymethyl-tetrahydrofuran, 2,5-dihydroxymethylfuran and 2,5-furandicarbaldehyde. Although the production of FDCA by chemical oxidative dehydration of C6 sugars and uses of FDCA are well known and poses technical barriers indicated in table 13 on page 26, for biotransformation—possibly enzymatic conversions—the position was unknown.

A process for the enzymatic preparation of FDCA is given in WO2009/023174. In this disclosure, a hydroxymethylfurfural species is oxidised with a chloroperoxidoreductase and hydrogen peroxide oxidised products having a carboxylic acid group at the C1 position of the hydroxymethylfurfural, in particular formylfuran carboxylic acid or FFCA. Results are e.g. shown in FIG. 1. In another embodiment, HMF is contacted with an oxidoreductase in the presence of an oxidizing substrate, whereby HMF is oxidized to at least one of diformylfuran or formylfuran carboxylic acid.

Disadvantages of the known process in WO2009/023174 are that the reaction requires hydrogen peroxide and that the product formed is a mixture of FDCA with two contaminating byproducts, hydroxymethylfuran carboxylic acid (HmFCA) and formylfuran carboxylic acid (FFCA). Consequently the yield of FDCA from HMF is reduced and additional recovery steps are needed to obtain FDCA in a substantially purified form.

In database EBI, Uniprot B2T4R9, a sequence of 577 aminoacids was identified that was inferred from homology as Glucose-Methanol-Choline oxidoreductase in the "complete sequence of chromosome 1 of *Burkholderia phytofirmans* PsJN.".

In database EBI, Uniprot B2JSZ0, a sequence of 576 aminoacids was identified that was inferred from homology as Glucose-Methanol-Choline oxidoreductase in the "complete sequence of plasmid 1 of *Burkholderia phymatum* STM815.".

In Deurzen, M. P. J. et al, J. Carbohydrate Chemistry 16(3), 299-309 (1997), the chloroperoxidase-catalysed oxidation of 5-Hydroxymethylfurfural is disclosed. The reaction proceeds with 60-74% selectivity to furan-2,5-dicarboxaldehyde (FDC). Byproducts were 5-hydroxymethyl-2-furancarboxylic acid (HFCA) and 5-formylfuran-2-carboxylic acid (FFCA).

SUMMARY

An object of the invention is to provide an oxidoreductase that can use molecular oxygen for redoxreactions. Another object is to provide an oxidoreductase that has broad reaction spectrum. Another object is to provide an oxidoreductase that has high regio-specificity. A further object of the invention is to provide a process for the production of FDCA wherein substantial amount of by-products can be avoided. A further object of the invention is to provide a process for the production of 5-hydroxymethyl-2-furancarboxylic acid (HMF acid) wherein substantial amount of by-products can be avoided. One or more of these objects are attained according to the invention.

The present invention provides polynucleotides encoding polypeptides having the oxidoreductase activity. Polynucleotides of the invention typically encode a polypeptide having oxidoreductase activity, in particular HmfH oxidoreductase activity.

According to the invention, there is thus provided a polypeptide having oxidoreductase activity which comprises the amino acid sequence set out in SEQ ID NO: 3 or an amino acid sequence encoded by the nucleotide sequence of SEQ ID NO: 4, or a variant polypeptide thereof having 45% or more sequence identity or more with the sequence of SEQ ID NO: 3.

These oxidoreductase polypeptides offer an enzymatic alternative to chemical oxidation routes to produce the value added compound FDCA, allowing mild reaction conditions (30° C., pH 7) and producing less waste. The oxidoreductase is a true oxidase, i.e. only molecular oxygen is required for the oxidation reaction omitting the requirement for regeneration of expensive cofactors. The enzyme offers broad reaction specificity and regio-specificity, oxidizing both alcohol and aldehyde groups to eventually carboxylic acid, irrespective whether these groups are on the C2 or C5 position of the furan backbone.

Also provided according to the invention is a vector, such as an expression vector, incorporating a polynucleotide sequence of the invention and a cell comprising a polypeptide, a polynucleotide or a vector, according to the invention.

The invention further provides a method for the preparation of a polypeptide having oxidoreductase activity, which method comprises cultivating a cell of the invention under conditions which allow for expression of said polypeptide and, optionally, recovering the expressed polypeptide and a polypeptide obtainable by such a method.

Another embodiment of the invention relates to an integrated process for the production of FDCA from fructose-(en)rich(ed) feed streams using a robust whole-cell biocatalyst.

DETAILED DESCRIPTION OF A PREFERRED EMBODIMENT

Figure 1:
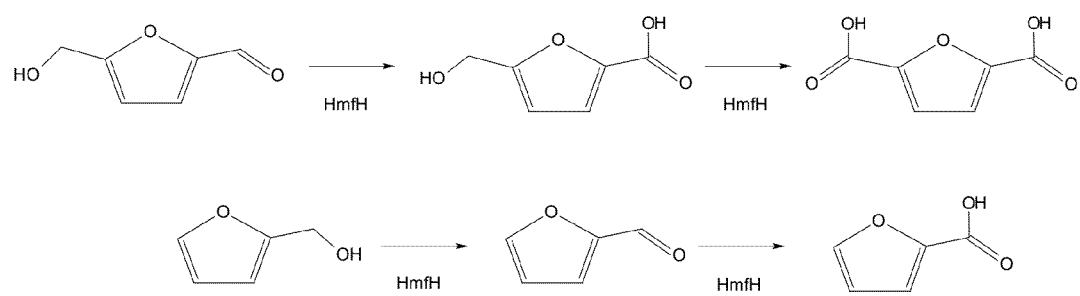
FIG. 1: Reaction scheme of oxidations catalysed by the HmfH oxidoreductase

SEQ ID NO: 1 sets out the DNA sequence of primer FN23:
5'-CG<u>GAATTC</u>CACATGACAAGGGGAGACCG-3'.
Underlined sequence indicates an EcoRI restriction site;

SEQ ID NO: 2 sets out the DNA sequence of primer FN24;
5'-CG<u>GAATTC</u>GCTTCGGTCTTCAACTCGGATG-3'.
Underlined sequence indicates an EcoRI restriction site;

SEQ ID NO: 3 sets out the amino acid sequence of HmfH
SEQ ID NO: 4 sets out the coding sequence of hmfH;

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

Broad reaction spectrum herein means the oxidoreductase can act as catalyst for the many different substrates e.g. HMF, HMFacid, HMF alcohol, furfural, furfuryl alcohol. Regiospecificity means it only oxidizes specific C-atoms.

Oxidoreductase Polypeptide

A polypeptide according to the invention having oxidoreductase activity comprises the amino acid sequence set out in SEQ ID NO: 3 or an amino acid sequence encoded by the nucleotide sequence of SEQ ID NO: 4, or a variant polypeptide thereof having at least 45% sequence identity with the sequence set out in SEQ ID NO: 3.

In one embodiment the variant nucleic acid molecule comprises a nucleotide sequence encoding a protein, comprising a substantially homologous nucleotide sequence of at least 66%, 70%, 75%, 80%, 85%, 90%, 91%, 92%, 93%, 94%, 95%, 96%, 97%, 98%, 99% or more homologous to the nucleotide sequence shown in SEQ ID NO: 4. In another embodiment the variant protein comprises a substantially homologous amino acid sequence of at least 45%, 50%, 55%, 60%, 65%, 70%, 75%, 80%, 85%, 90%, 91%, 92%, 93%, 94%, 95%, 96%, 97%, 98%, 99% or more homologous to the amino acid sequence shown in SEQ ID NO: 3.

An embodiment of the invention is a polynucleotide which comprises: (a) the nucleotide sequence set out in SEQ ID NO: 4; (b) a nucleotide sequence which hybridizes selectively with a polynucleotide being the reverse complement of SEQ ID NO: 4; (c) a nucleotide sequence having at least 66% sequence identity or more with the nucleotide sequence of SEQ ID NO: 4; (d) a fragment of a nucleotide sequence as defined in (a), (b) or (c) which is at least about 100 nucleotides in length; (e) a sequence which is degenerate as a result of the genetic code to a sequence as defined in any one of (a), (b), (c) or (d); (f) a nucleotide sequence which is the reverse complement of a nucleotide sequence as defined in (a), (b), (c), (d) or (e), or encodes a polypeptide; and to the relating polypeptides.

One embodiment is a nucleic acid construct comprising the polynucleotide, wherein GC content may be 56% or more, 58% or more, or from 58-65%. Further embodiment is a vector incorporating the polynucleotide sequence or a nucleic acid construct.

The terms "homology", "sequence identity" and the like are used interchangeably herein. For the purpose of this invention, it is defined herein that in order to determine the degree of sequence identity shared by two amino acid sequences or by two nucleic acid sequences, the sequences are aligned for optimal comparison purposes (e.g., gaps can be introduced in the sequence of a first amino acid or nucleic acid sequence for optimal alignment with a second amino or nucleic acid sequence). Such alignment may be carried out over the full lengths of the sequences being compared. Alternatively, the alignment may be carried out over a shorter comparison length, for example over about 20, about 50, about 100 or more nucleic acids/bases or amino acids.

The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The degree of identity shared between sequences is typically expressed in term of percentage identity between the two sequences and is a function of the number of identical positions shared by the sequences (i.e., % identity=number of identical positions/total number of positions (i.e. overlapping positions)×100). Preferably, the two sequences being compared are of the same or substantially the same length.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percentage identity between two amino acid sequences is determined using the Needleman and Wunsch (J. Mol. Biol. (48): 444-453 (1970)) algorithm which has been incorporated into the GAP program in the Accelrys GCG software package (available at http://www.accelrys.com/products/gcg/), using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the Accelrys GCG software package (available at http://www.accelrys.com/products/gcg/), using a NWSgapdna.CMP matrix and a gap weight of 40, 50, 60, 70, or 80 and a length weight of 1, 2, 3, 4, 5, or 6. In another embodiment, the percent identity two amino acid or nucleotide sequence is determined using the algorithm of E. Meyers and W. Miller (CABIOS, 4:11-17 (1989) which has been incorporated into the ALIGN program (version 2.0) (available at the ALIGN Query using sequence data of the Genestream server IGH Montpellier France http://vega.igh.cnrs.fr/bin/align-guess-.cgi) using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to oxidoreductase protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.ncbi.nim.nih.gov/.

As used herein, the term "selectively hybridizing", "hybridizes selectively" and similar terms are intended to describe conditions for hybridization and washing under which nucleotide sequences at least 66%, at least 70%, at least 75%, at least 80%, more preferably at least 85%, even more preferably at least 90%, preferably at least 95%, more preferably at least 98% or more preferably at least 99% homologous to each other typically remain hybridized to each other. That is to say, such hybridizing sequences may share at least 45%, at least 50%, at least 55%, at least 60%, at least 65, at least 70%, at least 75%, at least 80%, more preferably at least 85%, even more preferably at least 90%, more preferably at least 95%, more preferably at least 98% or more preferably at least 99% sequence identity.

A preferred, non-limiting example of such hybridization conditions is hybridization in 6× sodium chloride/sodium citrate (SSC) at about 45° C., followed by one or more washes in 1×SSC, 0.1% SDS at about 50° C., preferably at about 55° C., preferably at about 60° C. and even more preferably at about 65° C.

Highly stringent conditions include, for example, hybridization at about 68° C. in 5×SSC/5× Denhardt's solution/ 1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

In a typical approach, gene libraries constructed from other organisms, e.g. a bacterium, in particular from the microorganism family Trichomaceae, for example from the genus *Burkholderia* can be screened such as *Burkholderia phytofirmans*.

For example, *Burkholderia* strains can be screened for homologous oxidoreductase polynucleotides by Southern blot analysis. Upon detection of homologous DNA restriction fragments according to the invention, gene libraries can be constructed from chromosomal fragments of the same size from the appropriate strain, utilizing standard techniques well known to those of skill in the art. Alternatively, if the microorganism is a eukaryote, the mRNA transcript of the oxidoreductase HmfH can be identified by Northern hybridization and upon identification of the transcript, cDNA libraries can be prepared using total RNA isolated from the eukaryotic microorganism.

Homologous gene sequences can be isolated, for example, by performing PCR using two degenerate oligonucleotide primer pools designed on the basis of nucleotide sequences as taught herein.

The template for the reaction can be total chromosomal DNA from the strain known or suspected to express a polynucleotide according to the invention. The PCR product can be subcloned and sequenced to ensure that the amplified sequences represent the sequences of a new oxidoreductase nucleic acid sequence, or a functional equivalent thereof.

Alternatively the template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new oxidoreductase nucleic acid sequence, or a functional equivalent thereof.

The PCR fragment can then be used to isolate a full-length cDNA clone by a variety of known methods. For example, the amplified fragment can be labelled and used to screen a bacteriophage or cosmid cDNA library. Alternatively, the labelled fragment can be used to screen a genomic library.

PCR technology also can be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Another aspect of the invention pertains to vectors, including cloning and expression vectors, comprising a polynucleotide of the invention encoding a oxidoreductase protein or a functional equivalent thereof and methods of growing, transforming or transfecting such vectors in a suitable host cell, for example under conditions in which expression of a polypeptide of the invention occurs. As used herein, the term "vector" refers to a nucleic acid molecule capable of transporting another nucleic acid to which it has been linked.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

The vector into which the expression cassette or polynucleotide of the invention is inserted may be any vector which may conveniently be subjected to recombinant DNA procedures, and the choice of the vector will often depend on the host cell into which it is to be introduced.

A vector according to the invention may be an autonomously replicating vector, i. e. a vector which exists as an extra-chromosomal entity, the replication of which is independent of chromosomal replication, e. g. a plasmid. Alternatively, the vector may be one which, when introduced into a host cell, is integrated into the host cell genome and replicated together with the chromosome (s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

Vectors according to the invention may be used in vitro, for example for the production of RNA or used to transfect or transform a host cell.

A vector of the invention may comprise two or more, for example three, four or five, polynucleotides of the invention, for example for overexpression.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operably linked to the nucleic acid sequence to be expressed.

Within a vector, such as an expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell), i.e. the term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide.

The term "regulatory sequence" or "control sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990).

The term regulatory or control sequences includes those sequences which direct constitutive expression of a nucleotide sequence in many types of host cells and those which direct expression of the nucleotide sequence only in a certain host cell (e.g. tissue-specific regulatory sequences).

A vector or expression construct for a given host cell may thus comprise the following elements operably linked to each other in a consecutive order from the 5'-end to 3'-end relative to the coding strand of the sequence encoding the polypeptide of the first invention: (1) a promoter sequence capable of directing transcription of the nucleotide sequence encoding the polypeptide in the given host cell; (2) optionally, a signal sequence capable of directing secretion of the polypeptide from the given host cell into a culture medium; (3) a DNA sequence of the invention encoding a mature and preferably active form of a polypeptide having cellobiohydrolase activity; and preferably also (4) a transcription termination region (terminator) capable of terminating transcription downstream of the nucleotide sequence encoding the polypeptide.

Downstream of the nucleotide sequence according to the invention there may be a 3' untranslated region containing one or more transcription termination sites (e. g. a terminator). The origin of the terminator is less critical. The terminator can, for example, be native to the DNA sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG at the beginning and a termination codon appropriately positioned at the end of the polypeptide to be translated.

Enhanced expression of the polynucleotide of the invention may also be achieved by the selection of heterologous regulatory regions, e. g. promoter, secretion leader and/or terminator regions, which may serve to increase expression and, if desired, secretion levels of the protein of interest from the expression host and/or to provide for the inducible control of the expression of a polypeptide of the invention.

It will be appreciated by those skilled in the art that the design of the expression vector can depend on such factors as the choice of the host cell to be transformed, the level of expression of protein desired, etc. The vectors, such as expression vectors, of the invention can be introduced into host cells to thereby produce proteins or peptides, encoded by nucleic acids as described herein (e.g. oxidoreductase proteins, mutant forms of oxidoreductase proteins, fragments, variants or functional equivalents thereof, fusion proteins, etc.).

The vectors, such as recombinant expression vectors, of the invention can be designed for expression of oxidoreductaseproteins in prokaryotic or eukaryotic cells. For example oxidoreductase proteins can be expressed in bacterial cells such as *E. coli*, insect cells (using baculovirus expression vectors), filamentous fungi, yeast cells or mammalian cells. Suitable host cells are discussed further in Goeddel, *Gene Expression Technology: Methods in Enzymology* 185, Academic Press, San Diego, Calif. (1990). Representative examples of appropriate hosts are described hereafter.

Appropriate culture media and conditions for the above-described host cells are known in the art.

As set out above, the term "control sequences" or "regulatory sequences" is defined herein to include at least any component which may be necessary and/or advantageous for the expression of a polypeptide. Any control sequence may be native or foreign to the nucleic acid sequence of the invention encoding a polypeptide. Such control sequences may include, but are not limited to, a promoter, a leader, optimal translation initiation sequences (as described in Kozak, 1991, J. Biol. Chem. 266:19867-19870), a secretion signal sequence, a propeptide sequence, a polyadenylation sequence, a transcription terminator. At a minimum, the control sequences typically include a promoter, and transcriptional and translational stop signals.

A stably transformed microorganism is one that has had one or more DNA fragments introduced such that the introduced molecules are maintained, replicated and segregated in a growing culture. Stable transformation may be due to multiple or single chromosomal integration (s) or by (an) extra-chromosomal element(s) such as (a) plasmid vector(s). A plasmid vector is capable of directing the expression of polypeptides encoded by particular DNA fragments.

Expression may be constitutive or regulated by inducible (or repressible) promoters that enable high levels of transcription of functionally associated DNA fragments encoding specific polypeptides.

Isolation of the Oxidoreductase

The oxidoreductase or DNA material expressing the oxidoreductase may be isolated from an organism, preferably a microorganism that expresses the oxidoreductase. Preferably, the microorganism is capable of using HMF, but this is not necessary. The microorganism preferably is chosen from the group consisting of: *Cupriavidus, Burkholderia, Bradyhrizobium, Methylobacterium; Cupriavidus basisliensis, Burkholderia phytofirmans, Bradyhrizobium japonicum, Methylobacterium radiotolerans, Cupriavidus basisliensis* HMF14, *Burkholderia phytofirmans* PsJN, *Bradyhrizobium japonicum* USDA110, *Methylobacterium radiotolerans* JCM2831.

Most preferred oxidoreductase useful in the present invention is using a HMF and is an oxidoreductase isolated from *Cupriavidus basilensis* HMF 14 herein, deposited in accordance with the Budapest Treaty on International Recognition of the Deposits of Microorganisms for the Purpose of Patent Procedures at the DSMZ: *Cupriavidus basilensis* HMF14=DSM 22875, deposition date: Aug. 19, 2009, depositor TNO, Schoemakerstraat 97, 2628VK Delft, Netherlands.

We have thus isolated the HMF-utilizing bacterium, *Cupriavidus basilensis* strain HMF14, and identified the genes involved in the HMF degradative pathway. One of the genes (herein defined as hmfH) encoded a 579-amino acid, 62 kDa FAD-dependent oxidoreductase that was found to oxidize furfuryl alcohol, furfural, HMF, and 5-hydroxymethyl-furoic acid. The alcohol/aldehyde groups at C2 and C5, in these molecules were oxidized, without the requirement of additional nucleic acid construct encoding a reductase, though the presence of such activities may be advantageous. (see FIG. 1).

The present invention thus provides polynucleotides encoding polypeptides, e.g. enzymes having oxidoreductase (EC 1.1+EC 1.2 activities) activity. Enzymes are herein a subclass of polypeptides.

Oxidation Reaction

The oxidation reaction is herein one or more reaction of an oxidant with a furanic compound in the presence of the oxidoreductase of the invention and one or more co-enzymes (described herein below). The oxidation reaction may comprise one oxidation reaction step resulting in a product (e.g. the oxidation of HMF-acid to FDCA). Alternatively it may comprise more than one oxidation reaction step, each step resulting in an intermediate, where the last intermediate is the final product (e.g. the oxidation of HMF to FDCA). Examples of oxidation reactions are given in FIG. 1.

One oxidation reaction is the production of 2,5-furandicarboxylic acid (FDCA), wherein one or more furanic precursor of FDCA is converted to FDCA, by reaction with an oxidant in the presence of an oxidoreductase catalyst and one or more coenzyme, wherein the oxidoreductase catalyst comprises a polypeptide according to the invention. The furanic precursor of FDCA may be chosen from the group consisting of 5-hydroxymethylfurfural (HMF), 2,5-dihydroxymethyl furan (HMF alcohol) and 5-hydroxymethyl-2-furancarboxylic acid (HMF acid), preferably the furanic precursor is HMF. HMF may be obtained from one or more hexose sugars by heating in presence of acid, in a conventional way. The hexose sugars may be obtained from biomass. The oxidation reaction may also be a process for the production of 5-hydroxymethyl-2-furancarboxylic acid (HMF acid) wherein one or more furanic precursor of HMF acid is converted to HMF acid by reaction with an oxidant in the presence of an oxidoreductase catalyst and one or more coenzyme, wherein the oxidoreductase catalyst comprises a polypeptide to the invention. In one embodiment, the furanic precursor of HMF acid is chosen from the group chosen from 5-hydroxymethylfurfural (HMF) and 2,5-dihydroxymethyl furan (HMF alcohol). Other oxidation processes are possible.

The oxidation reactions are preferably conducted at relatively mild temperature, i.e. 10-80° C., more preferably 20-45° C., most preferably around from 25-40° C. The pH during the reaction is preferably pH 3 to 8, more preferably around pH 7. The reaction time is 6-18 hrs using atmospheric oxygen or pure oxygen and preferably the enzyme is reactive for longer times.

The reactor may be any suitable (aerated) bioreactor. It may be operated in batch, continuous or preferably in fed-batch.

Oxidation products such as FDCA, HMF-acid, etc. may be recovered from the reaction mixture by cooling/recrystallisation and separation of the crystallized oxidation product e.g. crystallized FDCA. However, other recovery methods are suitable, such as but not limited to acid precipitation and solvent extraction, as known in the art.

Optionally, the reaction takes place in the presence of a coenzyme. The coenzyme may be nicotinamide adenine dinucleotide (NAD+) and/or flavin adenine dinucleotide (FAD) and/or pyrroloquinoline quinolone (PQQ). A synergistic effect was found in the oxidation reaction of the invention with dehydrogenase activity, e.g. endogenous dehydrogenation activity found a cell in which the oxidation reaction takes place or present in a cell extract of such a cell. Process for the production of a polymer from one or more monomer, wherein one of the monomer is FDCA according Oxidant The oxidant during the reactions according to the invention may be any oxidant, preferably oxygen. The most economical source of oxygen is air. This is advantageous in that air is easily obtained from the atmosphere at no cost, no toxicity and no need to remove it after the reaction. Alternatively, one may employ a molecular oxygen liberating system. The oxygen-generating system may in principle be chosen from the various oxygen-generating systems which have been disclosed in the art. For example, one may use the catalase enzymes already present in the reaction mixture to generate oxygen from hydrogen peroxide.

Furanic Compounds

Furanic compounds are herein understood to be any compound having a furan group that may be oxidized to 2,5-furandicarboxylic acid or a precursor thereof. Preferred furan compounds include hydroxymethylfurfural (HMF), hydroxymethylfuran carboxylic acid (HMF acid), 2,5-dihydroxymethylfuran (HMF alcohol). The furan ring or any or its substitutable sidegroup may be substituted, e.g. with OH, C1-C10 alkyl, alkyl, allyl, aryl or RO— ether moiety, including cyclic groups, in the furan ring on any available position.

Expression of Oxidoreductase

Regardless of the exact mechanism utilized for expression of enzymes, it is contemplated that such expression is transferable by the introduction of genes encoding these enzymes into another host cell by methods known in the art. Genetic elements as herein defined include nucleic acids (generally DNA or RNA) having expressible coding sequences for products such as proteins, specifically enzymes, apoproteins or antisense RNA, which express or regulate expression of relevant enzymes. The expressed proteins can function as enzymes, repress or derepress enzyme activity or control expression of enzymes. Recombinant DNA encoding these expressible sequences can be either chromosomal (integrated into the host cell chromosome by, for example, homologous recombination) or extra-chromosomal (for example, carried by one or more plasmids, cosmids and other vectors capable of self replication). It is understood that the recombinant DNA utilized for transforming the host cell in accordance with this invention can include, in addition to structural genes and transcription factors, expression control sequences, including promoters, repressors and enhancers, that act to control expression or derepression of coding sequences for proteins, apoproteins or antisense RNA. For example, such control sequences can be inserted into wild-type host cells to promote overexpression of selected enzymes already encoded in the host cell genome, or alternatively they can be used to control synthesis of extrachromosomally encoded enzymes.

Recombinant DNA can be introduced into the host cell by any means, including, but not limited to, plasmids, cosmids, phages, yeast artificial chromosomes or other vectors that mediate transfer of genetic elements into a host cell. These vectors can include an origin of replication, along with cis-acting control elements that control replication of the vector and the genetic elements carried by the vector. Selectable markers can be present on the vector to aid in the identification of host cells into which genetic elements have been introduced.

Means for introducing genetic elements into a host cell (e.g. cloning) are well known to the skilled artisan. One can utilize an extrachromosomal multi-copy plasmid vector to insert the genetic elements in accordance with the present invention. Plasmid-borne introduction of the genetic element into host cells involves an initial cleaving of a plasmid vector with a restriction enzyme, followed by ligation of the plasmid and genetic elements encoding for the targeted enzyme species in accordance with the invention. Upon recircularization of the ligated recombinant plasmid, infection (e.g., packaging in phage lambda) or other mechanism for plasmid transfer (e.g., electroporation, microinjection, etc.) is utilized to transfer the plasmid into the host cell. Plasmids suitable for insertion of genetic elements into the host cell are well known to the skilled artisan.

Other gene cloning methods include, but are not limited to, direct integration of the genetic material into the chromosome. This can occur by a variety of means, including cloning the genetic elements described herein on non-replicating plasmids flanked by homologous DNA sequences of the host chromosome; upon transforming said recombinant plasmid into a host the genetic elements can be introduced into the chromosome by DNA recombination. Such recombinant strains can be recovered if the integrating DNA fragments contain a selectable marker, such as antibiotic resistance. Alternatively, the genetic elements can be directly introduced into the chromosome of a host cell without use of a non-replicating plasmid. This can be done by synthetically producing DNA fragments of the genetic elements in accordance to the present invention that also contain homologous DNA sequences of the host chromosome. Again if these synthetic DNA fragments also contain a selectable marker, the genetic elements can be inserted into the host chromosome.

Host Cell

Another embodiment of the invention is a cell comprising a polypeptide, a polynucleotide, a nucleic acid construct or a vector according to the invention. A host cell is a cell in which the a polypeptide, a polynucleotide, a nucleic acid construct or a vector can suitably be expressed.

The oxidoreductase may be favourably expressed in a host cell. The host cell according to the invention may be any host cell. The cell may be a prokaryote cell, a eukaryote cell, a plant cell or an animal cell. In such cell one or more genes may be deleted, knocked-out or disrupted in full or in part, wherein optionally one or more genes encode for protease. According to an embodiment, the host cell according to the invention is a eukaryotic host cell. Preferably, the eukaryotic cell is a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof. More preferably, the eukaryotic cell is a fungal cell, i.e. a yeast cell, such as *Candida, Hansenula, Kluyveromyces, Pichia, Saccharomyces, Schizosaccharomyces,* or *Yarrowia* strain. More preferably from *Kluyveromyces lactis, S. cerevisiae, Hansenula polymorpha, Yarrowia lipolytica* and *Pichia pastoris,* or a filamentous fungal cell. Most preferably, the eukaryotic cell is a filamentous fungal cell.

"Filamentous fungi" include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Thermoascus, Thielavia, Tolypocladium,* and *Trichoderma*.

Preferred filamentous fungal cells belong to a species of an *Aspergillus, Chrysosporium, Penicillium, Talaromyces* or *Trichoderma* genus, and most preferably a species of *Aspergillus niger, Aspergillus awamori, Aspergillus foetidus, Aspergillus sojae, Aspergillus fumigatus, Talaromyces emersonii, Aspergillus oryzae, Chrysosporium lucknowense, Trichoderma reesei* or *Penicillium chrysogenum*. When the host cell according to the invention is an *Aspergillus* host cell, the host cell preferably is CBS 513.88, CBS124.903 or a derivative thereof.

According to another embodiment, the host cell according to the invention is a prokaryotic cell. Preferably, the prokaryotic host cell is bacterial cell. The term "bacterial cell" includes both Gram-negative and Gram-positive microorganisms. Suitable bacteria may be selected from e.g. *Escherichia, Anabaena, Caulobacter, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, Gluconobacter oxydans, Caulobacter crescentus* CB 15, *Methylobacterium extorquens, Rhodobacter sphaeroides, Pseudomonas zeaxanthinifaciens, Pseudomonas putida, Pseudomonas putida* S12, *Paracoccus denitrificans, E. coli, C. glutamicum, Staphylococcus carnosus, Streptomyces lividans, Sinorhizobium melioti* and *Rhizobium radiobacter*.

Several strains of filamentous fungi are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL): e.g. the strains *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* ATCC44006. Also derivatives thereof may be used.

According to another embodiment, the host cell according to the invention is a prokaryotic cell. Preferably, the prokaryotic host cell is bacterial cell. The term "bacterial cell" includes both Gram-negative and Gram-positive microorganisms. Suitable bacteria may be selected from e.g. *Escherichia, Anabaena, Caulobacter, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces*. Preferably, the bacterial cell is selected from the group consisting of *B. subtilis, B. amyloliquefaciens, B. licheniformis, B. puntis, B. megaterium, B. halodurans, B. pumilus, G. oxydans, Caulobactert crescentus* CB 15, *Methylobacterium extorquens, Rhodobacter sphaeroides, Pseudomonas putida, Paracoccus zeaxanthinifaciens, Paracoccus denitrificans, E. coli, C. glutamicum, Staphylococcus carnosus, Streptomyces lividans, Sinorhizobium melioti* and *Rhizobium radiobacter*.

For specific uses of a compound produced in a host cell according to the invention, the selection of the host cell may be made according to such use. Where e.g. the compound produced in a host cell according to the invention is to be used in food applications, a host cell may be selected from a food-grade organism such as *Saccharomyces cerevisiae*. Specific uses include, but are not limited to, food, (animal) feed, pharmaceutical, agricultural such as crop-protection, and/or personal care applications.

The invention further relates to method for the preparation of a polypeptide having oxidoreductase activity, which method comprises cultivating a cell according to the invention under conditions which allow for expression of said polypeptide and, optionally, recovering the expressed polypeptide and to a polypeptide obtainable by a that method.

Feedstock

Agricultural crops naturally rich in fructans (e.g., topinambur or chicory roots) may be converted to an HMF-rich feedstock by conventional (combined) hydrolysis and thermochemical processing. The technology to generate HMF from fructose is well-established and robust. Also glucose-rich feedstock can be utilized, but the thermochemical formation of HMF proceeds more efficiently from fructose. Therefore, an additional enzymatic step can be included to convert glucose to fructose, using glucose isomerase. The latter process is well-established in food industry for producing high-fructose corn syrup (HFCS) from hydrolysed starch. To avoid competition with food applications, lignocellulosic hydrolysate would be the preferred feedstock for producing HMF/FDCA.

Biotransformation

For biotransformation of HMF to FDCA, a robust whole-cell biocatalyst is employed (free or immobilized cells) that expresses the *Cupriavidus basilensis* HMF oxidoreductase described herein before. A whole-cell biocatalyst has several advantages over an enzyme catalyst in this process: the HMF oxidoreductase is protected from chemical inactivation by the -highly reactive substrate and host-indigenous dehydrogenases can assist HMF oxidoreductase in the first two oxidation steps leading from HMF to (probably) the corresponding monoacid, which then is converted to the diacid by HmfH. Preferably, additional measures may be required to secure cofactor regeneration. The whole-cell biocatalyst should allow minimal processing of the HMF feed stream, i.e., preferably tolerate low pH, high T and the toxic compounds (among which the substrate) generated in the hydrolysis/thermochemical conversion of the feedstock. Pseudomonas putida S12 may qualify as a suitable host organism in view of its tolerance to diverse chemical stressors, its relatively wide pH range and the presence of indigenous dehydrogenases that assist HMF oxidoreductase resulting in a more efficient biotransformation of HMF to FDCA.

Alternative to the whole cell biocatalyst, in a similar way as the whole-cell biocatalyst, a cell lysate, purified enzyme, or an immobolized enzyme alone or as enzyme mixture may be used.

Product and Biomass Recovery

After biotransformation, the cells may be separated from the broth by established methods and re-used. FDCA may be recovered from the cell-free broth by acid precipitation and redissolved in a suitable organic solvent at elevated temperature. After dissolution, FDCA may be recovered by acid precipitation and solvent extraction, or other purification methods known in the art, at high purity in the di-acid form, in case this is desired.

Uses of FDCA

FDCA may be used as an alternative for terephtalate in the production of polyesters. It may also be used as a substrate for a large variety of valuable compounds. For instance it is a known substrate for the production of succinic acid, 2,5-bis (aminomethyl)-tetrahydrofuran, 2,5-dihydroxymethyl-tetrahydrofuran, 2,5-dihydroxymethylfuran and 2,5-furandicarbaldehyde. FDCA may be used in the production of coatings, e.g. in alkyd resin and thermoplastic coatings. It may also be used as a xylene equivalent in biofuels and as solvent.

FDCA may be esterified, and the esters may be used as plasticizers. It may converted to its diol, that may be used in PET-like polyesters and polyurethanes. Further it may be converted into its diamine, the diamine may be used as chain extender and the diamine may be converted into di-isocyanate, which can be used in the production of polyurethanes. Through the process according to the invention FDCA, and the products prepared from FDCA, can be made from biomass, including lignocellulosic biomass, through biotransformation.

EXAMPLES

General Methodology

Strains and plasmids *Cupriavidus basilensis* HMF 14, deposited at the DSMZ: *Cupriavidus basilensis* HMF14=DSM 22875, deposition date: Aug. 19, 2009 is a soil isolate that is able to use furans as a sole carbon source. *Pseudomonas putida* S12 (ATCC 700801) was used as the host for expression of HMF oxidoreductase. *Escherichia coli* DH5α (Invitrogen) was used for general cloning purposes. The pUCP22-derived *E. coli-P. putida* shuttle plasmid pJT'mcs (unpublished) was used for the expression of HMF oxidoreductase under control of the constitutive tac promotor. For replication in *E. coli,* the pUC origin of replication is employed; for replication in *P. putida,* the pRO1600 origin of replication is employed. Expression of the hmfH gene is driven from the constitutive tac promoter. The β-lactamase marker gene (bla) is used for antibiotic selection (ampicillin resistance) in *E. coli.* For antibiotic selection in *P. putida,* the gentamicin acetyltransferase marker gene (gmR) is used.

Figure 2:
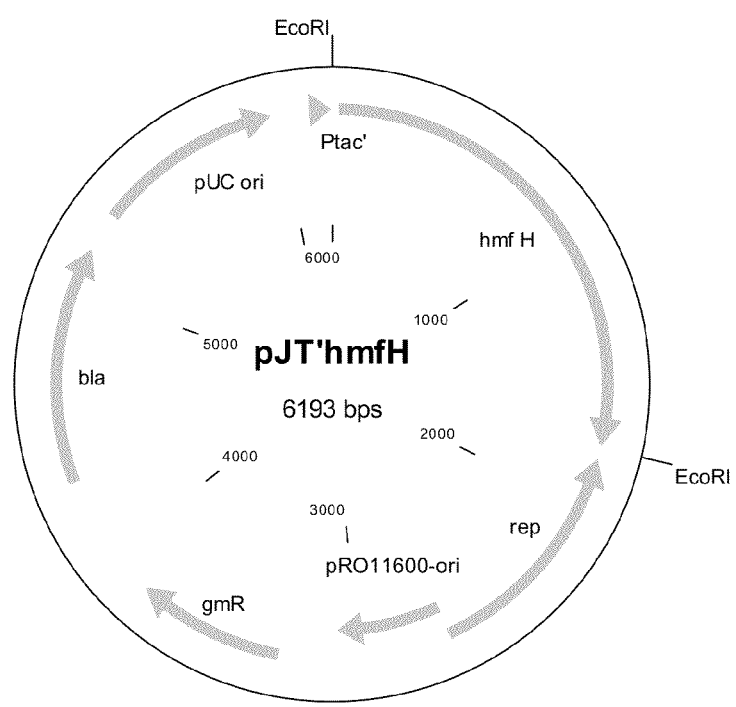
FIG. 2: Plasmid map of HmfH expression vector pJT'hmfH. Ptac', tac promotor; rep, gene encoding the pRO1600 replication protein; gmR, gentamicin resistance gene; bla, beta-lactamase; pRO1600-ori, origin of replication for *P. putida*; pUC ori, origin of replication for *E. coli*.
Figure 3A:
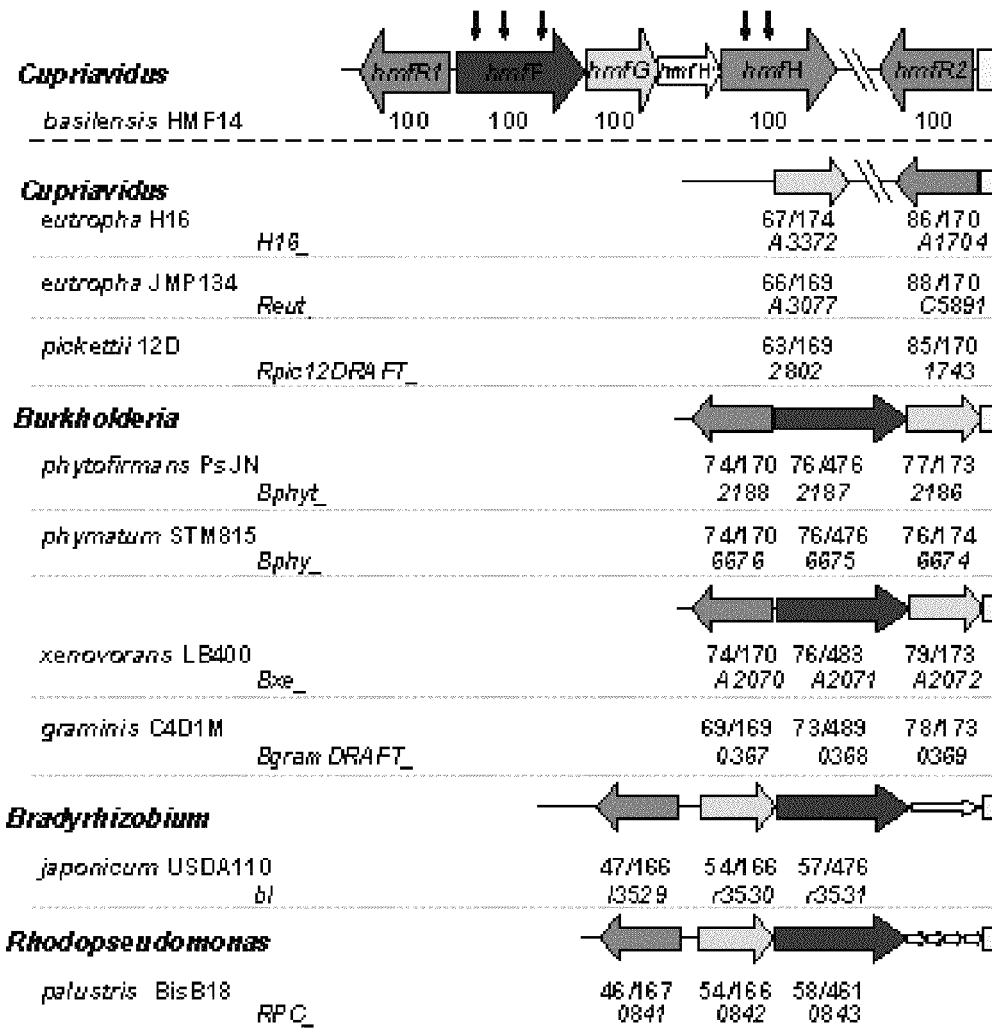
FIGS. 3A and 3B: Schematic representation of the genetic organization of the furfural and HMF metabolic genes in *C. basilensis* HMF14 and other species that were identified as potential furfural and/or HMF utilizers.
Figure 3B:
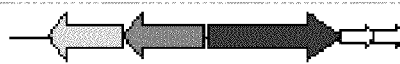
Figure 3C:
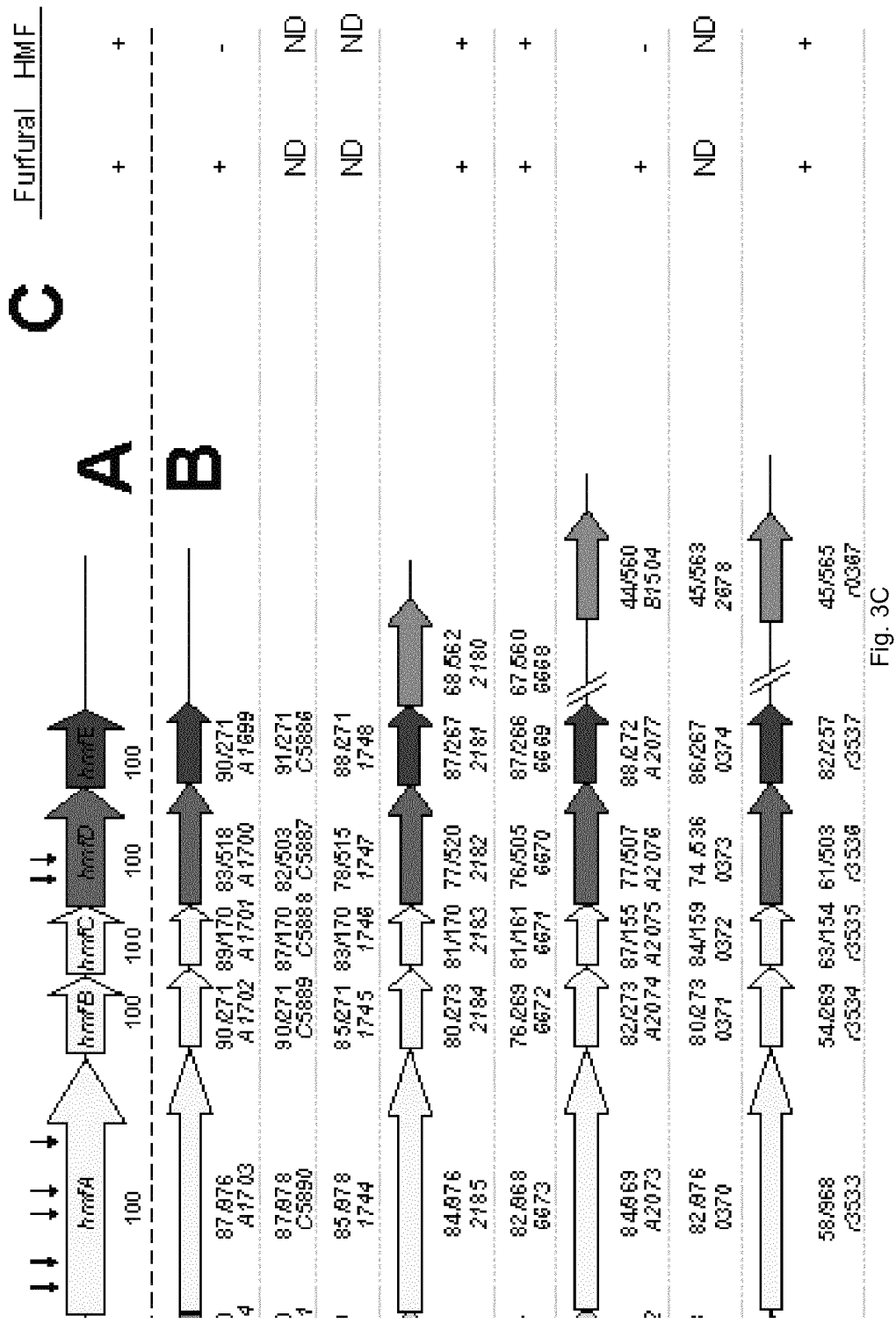
FIGS. 3C and 3D: Overview of growth phenotype of tested strains on mineral salts medium with either furfural or HMF (3 mM) as sole carbon source.
Figure 3D:
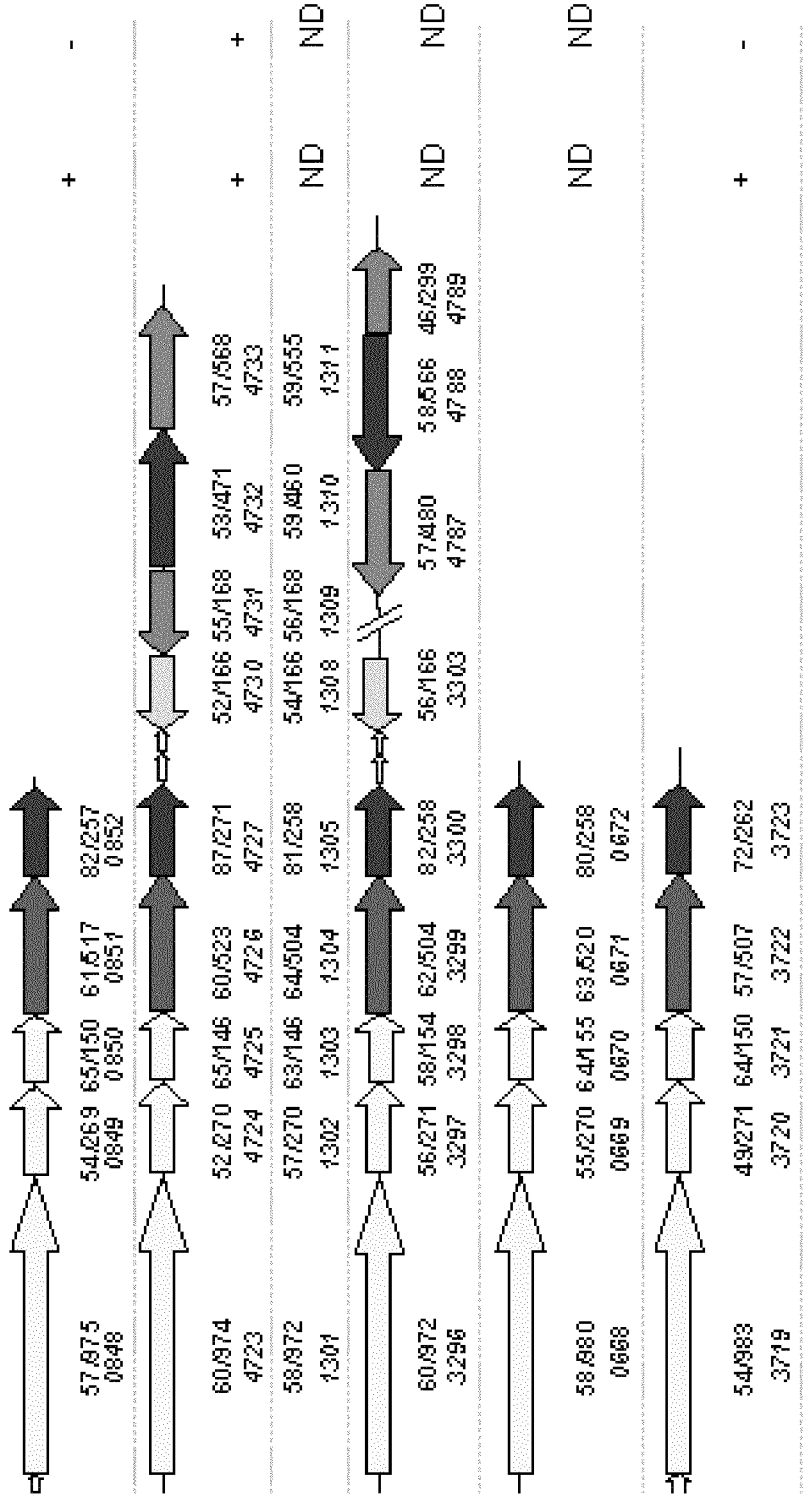

A Plasmid map of HmfH expression vector pJT'hmfH is given in FIG. 2. Ptac', tac promotor; rep, broad host range origin of replication; gmR, gentamicin resistance gene; bla, beta-lactamase; pUC ori, origin of replication for *E. coli.*

Media & Culture conditions Mineral salts medium (MM) was used as a defined medium. MM contained the following (per liter of demineralized water): 3.88 g of $K_2HPO_4$, 1.63 g of $NaH_2PO_4$, 2.0 g of $(NH_4)_2SO_4$, 0.1 g of $MgCl_2.6H_2O$, 10 mg of EDTA, 2 mg of $ZnSO_4.7H_2O$, 1 mg of $CaCl_2.2H_2O$, 5 mg of $FeSO_4.7H_2O$, 0.2 mg of $Na_2MoO_4.2H_2O$, 0.2 mg of $CuSO_4.5H_2O$, 0.4 mg of $CoCl_2.6H_2O$, and 1 mg of $MnCl_2.2H_2O$, supplemented with a carbon source as specified. Luria broth (L-broth: 10 g/l Bacto trypton (Difco), 5 g/l yeast extract (Difco), 5 g/l NaCl) was used as a complete medium for propagation of *P. putida* S12 and derivative strains, *C. basilensis* HMF14 and *E. coli* DH5α and derivatives. Solid L-broth was solidified with 2% (w/v) of agar (Difco).

For fed batch experiments, the initial batch phase was performed in 1 l of adapted mineral salts medium with the following composition: 3.88 g of $K_2HPO_4$, 1.63 g of $NaH_2PO_4$, 2.0 g of $(NH_4)_2SO_4$, 0.2 g of $MgCl_2.6H_2O$, 20 mg of EDTA, 4 mg of $ZnSO_4.7H_2O$, 2 mg of $CaCl_2.2H_2O$, 10 mg of $FeSO_4.7H_2O$, 0.4 mg of $Na_2MoO_4.2H_2O$, 0.4 mg of $CuSO_4.5H_2O$, 0.8 mg of $CoCl_2.6H_2O$, 2 mg of $MnCl_2.2H_2O$, 10 mg/L gentamicin and 100 mM glycerol. After depletion of the initial glycerol, the feed was started and controlled to allow maximum growth while maintaining glycerol as the limiting substrate in the culture. The feed solution contained (per l): 368.4 g glycerol and 10 g/L $MgCl_2.6H_2O$, and 12.6 g/L HMF.

Antibiotics: ampicillin (amp) was added to 100 μg/ml for *E. coli.* Gentamicin (gm) was added to 30 μg/ml in Luria broth and 10 μg/ml in mineral salts medium for *P. putida* S12. Antibiotics were purchased from Sigma-Aldrich.

Culturing: *P. putida* and *C. basilensis* were cultured at 30° C. *E. coli* was cultured at 37° C. Shake flask experiments on MM were performed in Boston bottles (Alltech applied sciences BV; Breda, The Netherlands) in a horizontally shaking incubator. Shake flask experiments on L-broth were performed in Erlenmeyer flasks with cotton plugs in a horizontally shaking incubator. Fed-batch experiments were performed in 1 l fermentors (New Brunswick Scientific) using a BioFlo110 controller. Initial batch fermentation was started with washed cells from an overnight preculture in 100 ml MM supplemented with 40 mM glycerol and 2 mM glucose. The initial stirring speed was set to 200 rpm and air was supplied to the head space at 1 l $min^{-1}$ using a M+W Instruments D-5111 mass-flow controller. Dissolved oxygen tension (DO) was continuously monitored with an InPro model 6900 probe (Mettler Toledo BV; Tiel, The Netherlands) and maintained at 30% air saturation by automatic adjustment of the stirring speed to a maximum of 1000 rpm. When the maximum stirring speed was reached, air was replaced with purified oxygen at a flow of 0.2 l $min^{-1}$ and the maximum stirring speed was set to 800 rpm. The pH was maintained at 7.0 by automatic addition of 25% $NH_4OH$ during initial batch phase, during the feed phase the pH was kept constant by automatic addition of 10 mM NaOH. The temperature was kept at 30° C.

Assays & Analytical methods: Cell dry weight (CDW) content of bacterial cultures was determined by measuring optical density at 600 nm ($OD_{600}$) using a Biowave Cell Density Meter (WPA Ltd) or a μQuant MQX200 universal microplate spectrophotometer (Biotek), using flat-bottom 96-well microplates (Greiner). An $OD_{600}$ of 1.0 corresponds to 0.56 g CDW/L (Biowave) or 1.4 g CDW/L (μQuant) for *P. putida.*

HPLC analyses: FDCA, HMF, HMF-alcohol and HMF-acid were analyzed by RP-HPLC (Agilent 1100 system) using a diode array detector set at 230 nm. The column used was a Zorbax Eclipse XDB-C8 (pore size of 80 Å, surface area of 180 $m^2$/g, Agilent) operated at 25° C. As eluent, a gradient of acetonitrile in 20 mM $KH_2PO_4$ (pH 2 or pH 6) with 1% acetonitrile was used at a flow of 1.2 ml/min, increasing from 0 to 5% in 3.5 min and from 5 to 40% in 2.5 min.

Preparation of cell extracts: Cell extracts of wildtype *C. basilensis* HMF14 or *P. putida* S12 transformants expressing HMF oxidoreductase were prepared from 50-ml late exponential growth phase cultures using MM supplemented with either 12 mM succinate (*C. basilensis* HMF14, $OD_{600}$≈1.5) or 20 mM glucose (*P. putida* S12, $OD_{600}$≈4). The cultures were harvested by centrifugation and resuspended in 3 ml of assay buffer. Cells were disrupted by sonication, using either a Branson sonifier (micro tip at pulse mode, output set at 3 and percentage duty cycle set to 40%; 3 cycles of sonication: 45 s of pulsing and 15 s pause) or a Sonics Vibra-Cell (Sonics&Materials, USA) (5 mm tapered microtip; pulse mode set to 1 min (0.5 s pulse, 2 sec pause). After sonication, debris was removed by centrifuging at 8228×g for 3 min at 4° C. The supernatant was desalted using a PD10 gel filtration column (GE healthcare) and used as cell extract for HMF oxidoreductase assays. Protein concentration was measured using Bradford reagent (Sigma-Aldrich).

HMF oxidoreductase assay: HMF oxidoreductase assays were performed in cell extracts of wildtype C. basilensis HMF14 or P. putida S12 transformants expressing the C. basilensis HMF14 HMF oxidoreductase. As a negative control, wildtype P. putida S12 or a C. basilensis HMF14 mutant was used that carried a transposon insertion in the hmfH gene. Cell extract was incubated with furfural, furfurylalcohol, HMF or HMF-acid at 30° C. under oxygenated conditions. The reaction mixture contained 1 ml cell extract, 976 µl oxygen-saturated MM, 20 µl of a 2 mM flavin adenine dinucleotide (FAD) solution and 4 µl of a 0.5 M stock of substrate (furfural, furfurylalcohol, HMF, or HMF acid. Samples were drawn at set intervals and the reaction was immediately stopped by addition of HCl to a final concentration of 1 M. Substrate and product concentrations in the samples were determined by HPLC. As an oxygen-depleted control, the different components of the reaction mixture were depleted of oxygen by a continuous stream of nitrogen gas and the same reaction mixture was incubated in headspace vials with a rubber stopper under nitrogen gas.

Chemicals: Analytical standard of FDCA was purchased from Immunosource B.V. (Halle-Zoersel, Belgium). 5-Hydroxymethyl-furoic acid (HMF acid) was purchased from Matrix Scientific (Columbia SC, United States). This compound was found to be highly esterified. Immediately prior to use, a 10 mM solution of the esterified HMF acid was boiled for two hours in 2 M $H_2SO_4$, cooled, and adjusted to pH 7.0 with NaOH after addition of 50 mM of phosphate buffer. All other chemicals were purchased from Sigma-Aldrich Chemie B.V. (Zwijndrecht, The Netherlands).

Molecular and genetic techniques: Genomic DNA was isolated using the DNeasy tissue kit (QIAGEN). Plasmid DNA was isolated with the QIAprep spin miniprep kit (QIAGEN). Agarose-trapped DNA fragments were isolated with the QIAEXII gel extraction kit (QIAGEN).

PCR reactions were performed with Accuprime Pfx polymerase (Invitrogen) according to the manufacturer's instructions. Primers used to amplify HMF oxidoreductase from genomic DNA of C. basilensis HMF14 were FN23: 5'-CG<u>GAATTC</u>CACATGACAAGGGGAGACCG-3' (SEQ ID NO: 1) and FN24; 5'-CG<u>GAATTC</u>GCTTCGGTCTTCAACTCGGATG-3' (SEQ ID NO: 2). Underlined sequences indicate an EcoRI restriction site.

Plasmid DNA was introduced into electrocompetent cells using a Gene Pulser electroporation device (BioRad).

Chromosomal DNA flanking the transposon was identified by standard methods known in the art {Ausubel, F. M. et al. Current protocols in molecular biology (Green publishing association, New York; 1987)} and the sequence of the complete genetic loci were obtained by primer walking. Oligonucleotide synthesis and DNA sequencing were performed by MWG Biotech AG (Germany).

Other standard molecular biology techniques were performed according to Sambrook and Russell {Sambrook, J, Russel, D. W. Molecular cloning; a laboratory manual (Cold spring Harbor Laboratory Press, New York: 2001)

Example I

FDCA Production in Cell Extract of C. Basilensis HMF14

When cell extract of C. basilensis, from a late log phase preculture ($OD_{600} \approx 1.5$) grown on MM supplemented with 12 mM succinate and 3 mM HMF, was incubated with either HMF, or HMF acid, formation of FDCA was observed.

When HMF was used as the substrate, a fast transient accumulation of HMF-acid an HMF-alcohol was observed concurrent with FDCA formation. In desalted cell extract the HMF-acid concentration decreased at a slower rate and FDCA production was slower compared to crude cell extract. Since FDCA was produced in desalted cell extract as well as in crude cell extract, the conversion of HMF to FDCA appeared not to involve cofactors. Nevertheless, cofactors or other low-molecular weight components from crude cell extract appeared to have a synergistic effect on FDCA formation. When HMF-acid was added as the substrate, immediate formation of FDCA was observed in both crude and desalted cell extract. It was furthermore demonstrated that the presence of oxygen was required for FDCA formation as no FDCA was produced under anaerobic conditions. Stoichiometric conversion of HMF acid to FDCA was observed.

Example II

Isolation and Characterization of the hmfH Gene Encoding HMF Oxidoreductase

The hmfH gene was found to encode a 62 317 Da protein belonging to the FAD-dependent glucose-methanol-choline (GMC) oxidoreductase family. This enzyme was shown to have the ability to oxidize HMF-acid to furan-dicarboxylic acid (FDCA). In addition, the enzyme also accepted HMF as the substrate, which was oxidized, via HMF-acid, to FDCA. The highest homology with HmfH in the non-redundant NCBI database was found with the GMC oxidoreductase of Burkholderia phytofirmans PsJN (locus tag Bphyt_2180; 68% identity over a 562-amino acid stretch). Based on the sequence data of the HMF/furfural operon of C. basilensis HMF14 other potential HMF/furfural degraders were identified. Selected strains were tested for growth on mineral salts medium with either HMF or furfural as the sole carbon source. The strains that were able to grow on HMF had an hmfH orthologue encoding oxidoreductases that are between 45 and 68% identical to HmfH. One strain (Burkholderia xenovorans LB400) was unable to utilize HMF although its oxidoreductase was 44% identical to HmfH.

FIG. 3 gives a schematic representation of the genetic organization of the furfural and HMF metabolic genes in C. basilensis HMF14 (A) and other species (B) that were identified as potential furfural and/or HMF utilizers. Colours correspond to enzyme activities in FIG. 1. Bold numbers (x/y) below arrows indicate the percentage identity (x) to the corresponding C. basilensis HMF14 protein in a y amino-acid stretch. Orthologous genes were identified by BLASTx homology searches in the non-redundant protein database of the National Center for Biotechnology Information. Hits for the furfural cluster were defined as relevant when orthologues for hmfA, B, C, D and E were present in a single genome, with the hmfA orthologue encoding an enzyme that was at least 50% identical to HmfA. The same criterion was used to define hmfF and hmfG orthologues, whereas 40% identity to HmfH was used as the criterion for hmfH orthologues. Numbers in italics indicate genome locus tags of the indicated strain. White arrows depict genes with no metabolic function. C: Overview of growth phenotype of tested strains on mineral salts medium with either furfural or HMF (3 mM) as the sole carbon source. ND: not determined.

In the figures there are given the Nucleotide sequence of the open reading frame encoding HMF-oxidoreductase HmfH (FIG. 4) and the deduced amino acid sequence (FIG. 3).

Example III

Cloning of hmfH in *P. Putida* S12 and Expression of the Encoded Oxidoreductase

The hmfH gene encoding HMF oxidoreductase was cloned into expression vector pJT'mcs. The PCR fragment obtained with primers FN23 and FN24 on *C. basilensis* HMF14 genomic DNA was digested with EcoRI (Fermentas). The digested fragment was ligated into EcoRI-digested and FastAP (Fermentas)-treated pJT'mcs vector, yielding HmfH expression plasmid pJT'hmfH. The correct orientation of the hmfH insert was verified by means of control digestion and by nucleotide sequencing known in the art. Expression of HMF oxidoreductase was demonstrated in cell extract of *P. putida*_pJT'hmfH grown in MM+20 mM glucose and 10 mg/l gentamicin ($OD_{600} \approx 4$) by the formation of FDCA using HMF or HMF acid as the substrate (Table 1).

TABLE 1

Formation of FDCA from HMF or HMF acid in cell extract of P. putida_pJT'hmfH. As control, cell extract of P. putida S12 harbouring the empty expression vector pJT'mcs was used.

| cell extract | Oxygen | |
| --- | --- | --- |
| | yes | no |
| desalted | + | − |
| not desalted | + | − |
| control, desalted | − | − |
| control, not desalted | − | − |

These results confirmed that the formation of FDCA only occurs in the presence of oxygen, and is catalyzed by the hmfH-encoded oxidoreductase. When HMF was used as the substrate, transient accumulation of HMF-acid was observed both in desalted and crude cell extract. The formation of HMF-acid in desalted cell extract (low-MW cofactors removed) indicated HmfH not only oxidized HMF-acid to FDCA, but can also oxidize HMF to its mono-carboxylic acid form.

In addition to HmfH, also apparently unspecific dehydrogenases that are indigenous to *P. putida* S12 can form HMF acid from HMF (Table 2), provided that the reducing equivalents are not removed by desalting. The aldehyde reductase/alcohol dehydrogenase activity was NADH/NAD+ dependent whereas the aldehyde dehydrogenase activity could be supported by a combination of the two artificial electron carriers, PMS and DCPIP, in which PMS is the primary electron carrier and DCPIP is the final electron acceptor. Similar activities were also observed in cell extract of *C. basilensis* HMF 14.

TABLE 2

Non-specific HMF-dehydrogenase activities measured in cell extract of wild type *P. putida* S12.

| Enzyme activity | Substrate | Product | Cofactor | P. putida S12 |
| --- | --- | --- | --- | --- |
| aldehyde reductase | HMF | HMF alcohol | NADH | 1106 |
| alcohol dehydrogenase | HMF alcohol | HMF | $NAD^+$ | ND |
| aldehyde dehydrogenase | HMF | HMF acid | PMS/DCPIP | 8 |

ND: not determined for lack of commercially available substrate. Activities depicted in U g$^{-1}$ protein.
PMS/DCPIP: phenazine methosulphate/2,6-dichlorophenol-indophenol.

Figure 4:
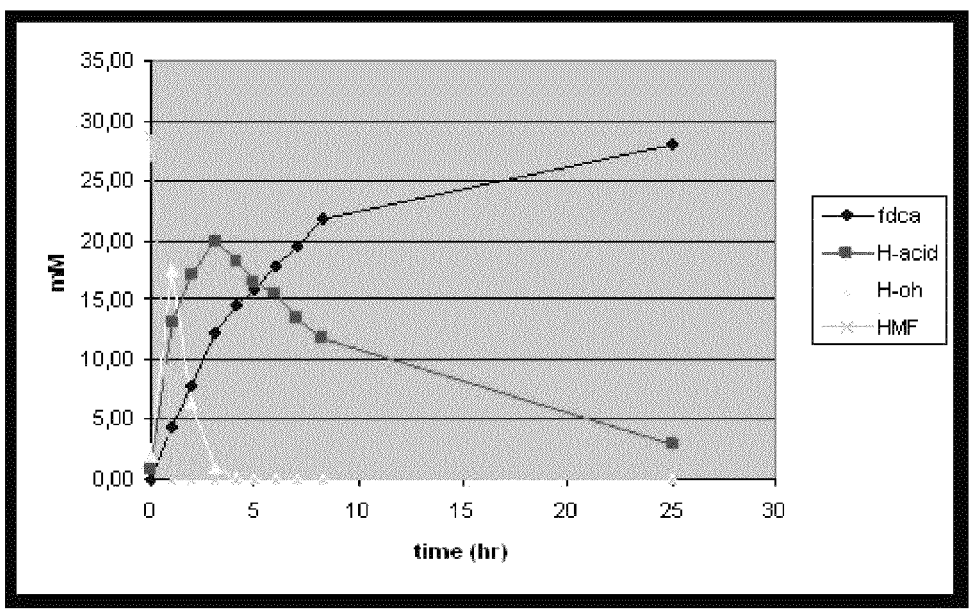
FIG. 4: Formation of FDCA, HMF-alcohol (H-oh) and HMF-acid (H-acid) from HMF in crude cell extract of *P. putida* S12 pJT'hmfH.

Formation of FDCA, HMF-alcohol (H-oh) and HMF-acid (H-acid) from HMF in crude cell extract of *P. putida* S12 pJT'hmfH is shown in FIG. 4. FIG. 4 illustrates the synergistic effects of endogenous dehydrogenases and HmfH in *P. putida* S12 pJT'hmfH cell extract. First, a rapid decrease in HMF was observed concomitant with the formation of HMF-alcohol which was probably catalysed by aldehyde reductase. At the same time, also HMF-acid (likely via aldehyde dehydrogenase) and FDCA (via HmfH) started to accumulate. Immediately after formation, HMF-alcohol disappeared, probably through re-oxidation to HMF, HMF-acid and FDCA. Only HMF-acid showed significant accumulation prior to being oxidized (almost) completely to FDCA in a 25-h time span. These results suggest that the oxidation of HMF-acid to FDCA was the rate-limiting step in this cell-free system.

Example IV

Whole-Cell Transformation of HMF to FDCA with *P. Putida* S12 Expressing HmfH

Because endogenous dehydrogenases of *P. putida* S12 can act synergistically with HmfH in the oxidation of HMF to FDCA by providing an additional means of generating HMF-acid from HMF, a whole-cell biotransformation process of HMF to FDCA may have advantages over an enzymatic process. To investigate this possibility, resting cells, growing cells and disrupted cells were tested for HMF to FDCA production.

Shake flask cultures were grown in 150 ml MM+40 mM glycerol and 2 mM glucose supplemented with 10 mg/L gentamicin in 1-L Erlenmeyer flasks. Cells were harvested at the end of the log phase ($OD_{600} \approx 4$), washed and concentrated in MM supplemented with 19.4 g/L of $K_2HPO_4$, 8.15 g/L of $NaH_2PO_4$, 40 mM glycerol and 10 mg/L gentamicin. Aliquots (10 ml) of the concentrated cell suspensions (corresponding to 1.65 g of CDW) were incubated with HMF in 250 ml Erlenmeyer flasks and samples were drawn at regular intervals for analysis of FDCA. For resting cells, glycerol was omitted from the resuspension medium and the disrupted cells were obtained by sonication.

As observed previously, HMF was rapidly converted into HMF-alcohol and HMF acid, followed by a decline of HMF acid and concurrent formation of FDCA. Both FDCA production rates and HMF acid decrease rates are presented in Table IV-a, for two concentrations of HMF tested.

TABLE 3

Production of FDCA from HMF and HMF-acid decrease rate using growing cells, resting cells, and sonified cells of *P. putida* S12 pJT'hmfH, at different starting concentrations of HMF.

| concentration HMF (mM) | HMF-acid decrease rate (μmol/gCDW/h) | | | FDCA production rate (μmol/gCDW/h) | | |
|---|---|---|---|---|---|---|
| | growing cells | resting cells | disrupted cells | growing cells | resting cells | disrupted cells |
| 25 | 194 ± 10[b] | 120[a] | 73[a] | 145 ± 3.5[b] | 115[a] | 115[a] |
| 50 | 377 ± 27[b] | ND[c] | ND[c] | 450 ± 80[b] | ND[c] | ND[c] |

[a] Incomplete conversion of HMF-acid to FDCA was observed.
[b] Duplicate experiments; the variation is the maximum deviation from the mean of two independent experiments.
[c] ND = not determined Table 3 shows that FDCA production was more efficient with growing cells of *P. putida* S12 expressing HmfH. The overall FDCA production rate, conversion efficiency, as well as the HMF-acid decrease rate were higher for the growing cell-incubations. In addition, the FDCA production rate was dependent on the initial concentration of HMF suggesting that the system was not saturated.

Example V

Fed-Batch FDCA Production from HMF with *P. Putida* S12 Expressing HmfH

Production of FDCA was found to be most efficient with growing cells of *P. putida* S12 expressing HmfH. Therefore, fed-batch experiments were performed to demonstrate the production of FDCA with whole cells of *P. putida* S12 pJT'hmfH.

Figure 5:
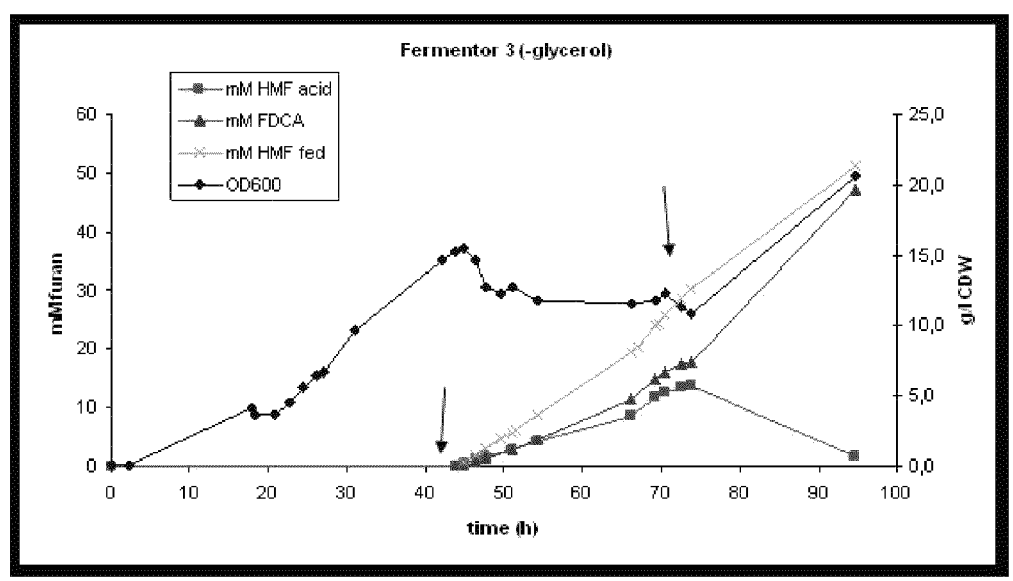
FIG. 5: Formation of HMF acid and FDCA in a fed-batch culture of *P. putida*_pJT'hmfH. The left-hand arrow indicates the start of the HMF feed; the right-hand arrow indicates the addition of glycerol to the feed.

In the initial phase, *P. putida*_pJT'hmfH was cultured on MM with a feed of glycerol to a cell density of 13 g CDW/l. At the end of this phase, the HMF feed was started, administering HMF at a rate of 0.8 mmol/l/h. Without glycerol-co-feeding, HMF-acid and FDCA were formed at an equal rate of 0.41 mmol/l/h (See FIG. 5). Subsequently the feed was replaced with a solution containing 0.21 M HMF and 4 M glycerol, fed at approximately 5 ml/h. With this glycerol co-feeding, the HMF-acid concentration rapidly declined while the formation of FDCA continued at approximately the same rate (FIG. 5). The experiment was stopped when a total amount of 44.6 mmol HMF had been added to the fed batch. Results showed almost complete conversion (i.e., 96.5% efficiency) to FDCA.

Figure 6:
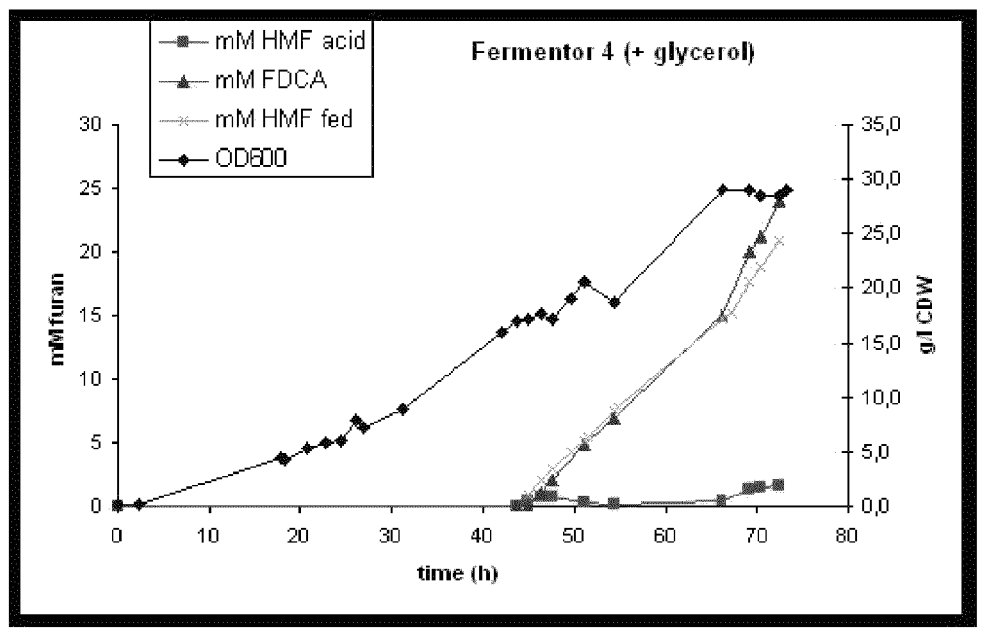
FIG. 6: Formation of HMF acid and FDCA in a fed-batch culture of *P. putida*_pJT'hmfH. The arrow indicates the start of the combined HMF and glycerol feed.

In a similar experiment glycerol was co-fed at an average rate of 0.7 mmol/l/h along with HMF. In this fed-batch culture, no accumulation of the HMF acid intermediate was observed and all HMF was converted directly into FDCA (FIG. 6).

Example VI

Purification of FDCA from Fermentation Broth

The solubility of FDCA at a pH of 1.0 was found to be around 1.5 g/l in water. This property was employed advantageously for recovery of the FDCA product from the fermentation broth. After removal of cells by centrifugation (9500×g for 5 min), approximately 10 ml 96% $H_2SO_4$ was added to 100 ml of the clarified broth at room temperature under continuous stirring until pH 1, in order to precipitate FDCA. The precipitate was recovered by centrifugation at 8228×g for 10 min and the air-dried pellet was redissolved in methanol at 60° C. Upon removal of undissolved debris by filtration through a preheated 0.22-μm filter, the filtrate was analyzed for purity by HPLC. The purity of the FDCA recovered from the fermentation broth by the above procedure was approximately 65%. Further purification of FDCA can be achieved using methods well known in the art.

Example VII

Fed-Batch FDCA Production from HMF with *P. Putida* S12 Expressing HmfH

A second fed-batch FDCA production experiment was performed in order to increase FDCA titer and productivity with whole cells of *P. putida* S12 pJT'hmfH.

Figure 7A:
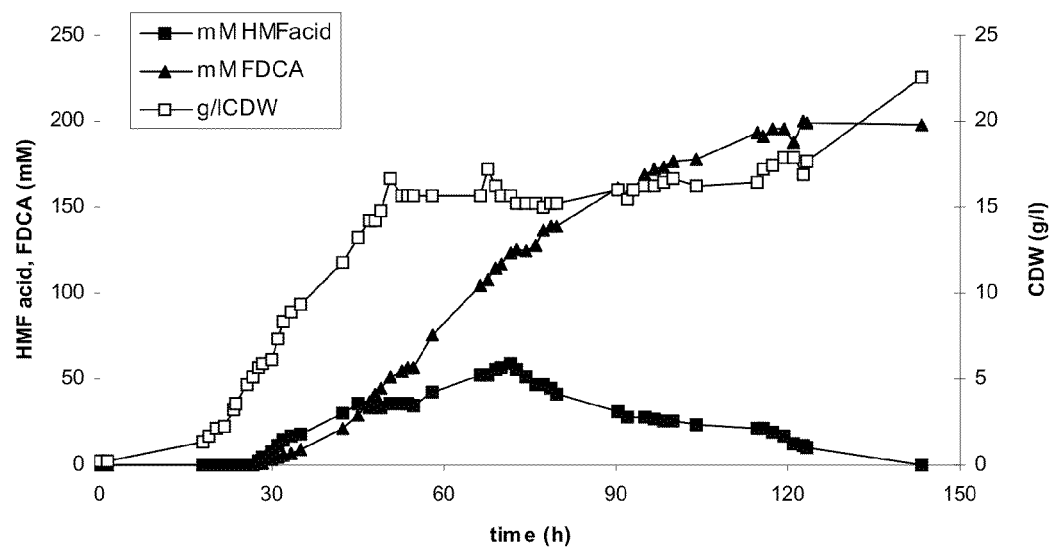
FIG. 7a: Concentrations of HMF acid, FDCA and biomass in the fed-batch fermentation of example VIII. 7b: feed rates of glycerol and HMF in the fed-batch fermentation of example VIII.
Figure 7B:
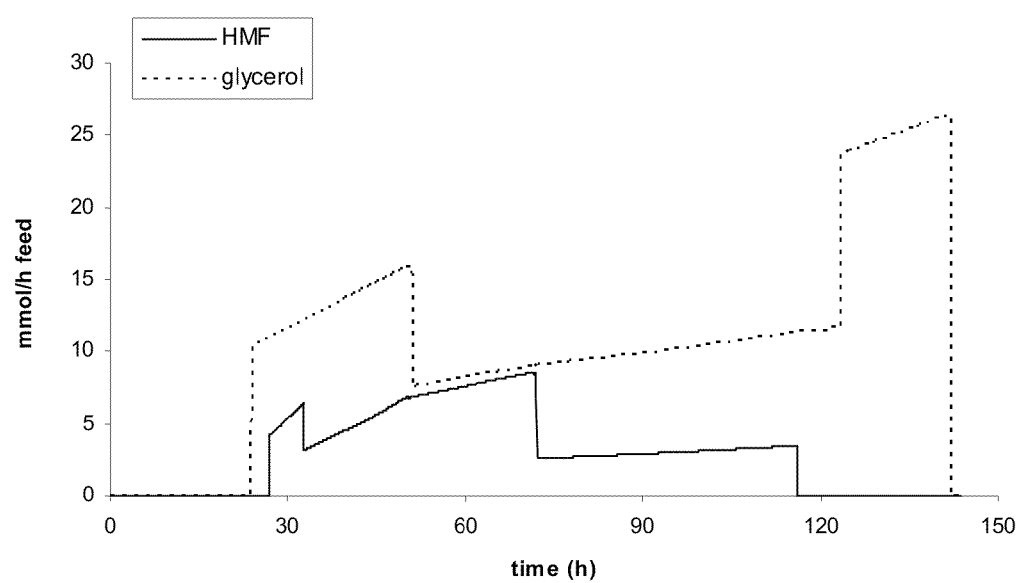

In the initial batch phase, *P. putida*_pJT'hmfH was cultured on MM until the initial glycerol was depleted ($OD_{600}$≈8) after 23.2 hours of fermentation. At this point the glycerol feed was started at a rate that allowed a biomass increase of approximately 0.45 g CDW/l/h. After 50.7 hours of fermentation, the glycerol feed was decreased to a rate that allowed a biomass increase of approximately 0.045 g CDW/l/h. After 123.4 hours of fermentation, the glycerol feed was increased to a rate that allowed a biomass increase of approximately 0.25 g CDW/l/h until the end of the fermentation. Over this period, a HMF feed was applied. The HMF feed started at a rate of 0.65 mmol/h/g CDW after 26.7 hours of fermentation, leading to the accumulation of both HMF acid and FDCA. The HMF feed rate was decreased to 0.28 mmol/h/g CDW after 33.3 hours of fermentation, decreased further to 0.09 mmol/h/g CDW after 72.8 hours of fermentation and stopped after 117.4 hours of fermentation. The decreasing HMF feed led to a gradual decrease of the HMF acid concentration in the fermentor, while the FDCA concentration continued to increase. The fermentation was stopped when no more HMF acid could be detected. At this point 188 mmol of HMF was added to the fermentor, leading to the production of approximately 182 mmol FDCA (i.e., 97% efficiency) at a concentration of 30.8 g/l. FIG. 7a shows the formation of biomass, HMF acid and FDCA in the fed-batch culture of *P. putida*_pJT'hmfH. FIG. 7b shows the feed rates of glycerol and HMF of the same culture.

Example VIII

Purification of FDCA from Fermentation Broth

The solubility of FDCA at a pH of 0.5 was found to be around 0.4 g/l in water. Since this concentration remains in solution after precipitation, the increased titer obtained in example VIII leads to a much reduced loss of product from purification by precipitation.

After removal of cells by centrifugation (9500×g for 15 min), 500 ml of the clarified broth was boiled for 3 minutes to precipitate proteins and centrifuged for 20 min at 9500×g. Approximately 50 ml 96% $H_2SO_4$ was added to the supernatant at 4° C. under continuous stirring until pH 0.5, in order to precipitate FDCA. The precipitate was recovered by centrifugation at 8228×g for 20 min, washed once with 250 ml of water and centrifuged again at 8228×g for 20 min. The resulting pellet was air-dried and then dissolved in approximately 1200 ml tetrahydrofuran (THF) at 30° C. Upon removal of undissolved debris by filtration, the clarified THF solution was evaporated under vacuum at 50° C. until 11.8 g of dry FDCA powder remained with a high purity (>99%), which is 78% of the FDCA initially in the fermentor broth. If needed, the purification of FDCA can be further optimized using methods well known in the art.

The invention claimed is:

1. An isolated cell comprising an expression construct for expression of a heterologous nucleotide sequence encoding an oxidoreductase having an amino acid sequence with at least 95% identity with the amino acid sequence of SEQ ID NO: 3, wherein, said expression construct is expressible in said cell and expression thereof of said oxidoreductase confers to or increases in the cell the ability to oxidize at least one of 5-hydroxymethylfurfural (HMF) and 5-hydroxymethyl-2-furancarboxylic acid (HMF acid) to 2,5-furandicarboxylic acid (FDCA), as compared to a corresponding wild type cell lacking the expression construct.

2. The cell according to claim 1, wherein said cell is a bacterium selected from the group consisting of *Escherichia, Anabaena, Caulobacter, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces* genus; or *B. subtilis, B. amyloliquefaciens, B. licheniformis, B. puntis, B. megaterium, B. halodurans, B. pumilus, G. oxydans, Caulobacter crescentus* CB 15, *Methylobacterium extorquens, Rhodobacter sphaeroides, Pseudomonas putida, Paracoccus zeaxanthinifaciens, Paracoccus denitrificans, E. coli, C. glutamicum, Staphylococcus carnosus, Streptomyces lividans, Sinorhizobium melioti* and *Rhizobium radiobacter* species.

3. The cell according to claim 1, wherein said cell is a yeast cell selected from the group consisting of *Candida, Hansenula, Kluyveromyces, Pichia, Saccharomyces, Schizosaccharomyces,* or *Yarrowia* genus; or *Kluyveromyces lactis, S. cerevisiae, Hansenula polymorpha, Yarrowia lipolytica* and *Pichia pastoris* species or a *filamentous* fungal cell from the group *Aspergillus, Chrysosporium, Penicillium, Talaromyces* or *Trichoderma* genus; or *Aspergillus niger, Aspergillus awamori, Aspergillus foetidus, Aspergillus sojae, Aspergillus fumigatus, Talaromyces emersonii, Aspergillus oryzae, Chrysosporium lucknowense, Trichoderma reesei* or *Penicillium chrysogenum* species.

4. A method for preparing a polypeptide having oxidoreductase activity, which method comprises cultivating the cell of claim 1 under conditions which allow for expression of said polypeptide and, optionally, recovering an expressed polypeptide.

5. A process for producing 2,5-furandicarboxylic acid (FDCA), wherein at least one furanic precursor of FDCA is converted to FDCA, by reaction with an oxidant in the presence of an oxidoreductase catalyst and optionally at least one coenzyme, where in the oxidoreductase catalyst comprise the oxidoreductase of claim 1.

6. The process of claim 5, wherein said furanic precursor of FDCA is selected from the group consisting of 5-hydroxymethylfurfural (HMF), 2,5-dihydroxymethyl furan (HMF alcohol) and 5-hydroxymethyl-2-furancarboxylic acid (HMF acid), and wherein optionally said furanic precursor is HMF.

7. The process of claim 6, wherein said precursor is HMF and HMF is obtained from at least one hexose sugar by heating in presence of acid, wherein optionally at least one hexose sugar is obtained from biomass.

8. A process for producing 5-hydroxymethyl-2-furancarboxylic acid (HMF acid) wherein at least one furanic precursor of HMF acid is converted to HMF acid by reaction with an oxidant in the presence of an oxidoreductase catalyst and optionally at least one coenzyme cofactor, wherein the oxidoreductase catalyst is a cell free extract of the cell of claim 1, or a whole cell biocatalyst being the cell of claim 1.

9. The process of claim 8, wherein the at least one furanic precursor of HMF acid is selected from the group consisting of 5-hydroxymethylfurfural (HMF) and 2,5-dihydroxymethyl furan (HMF alcohol).

10. The process of claim 5, wherein said coenzyme is nicotinamide adenine dinucleotide (NAD+) and/or pyrroloquinoline quinolone (PQQ) and/or flavin adenine dinucleotide (FAD).

11. A process for the production of a polymer from at least one monomer, wherein said at least one monomer is FDCA obtained in the process of claim 5.

12. An expression construct for expression of a heterologous nucleotide sequence encoding an oxidoreductase in a cell, wherein the oxidoreductase has an amino acid sequence with at least 95% identity with the amino acid sequence of SEQ ID NO: 3, wherein, said expression construct when said oxidoreductase is expressed thereof in said cell confers to or increases in the cell the ability to oxidize at least one of 5-hydroxymethylfurfural (HMF) and 5-hydroxymethyl-2-furancarboxylic acid (HMF acid) to 2,5-furandicarboxylic acid (FDCA), and wherein at least one regulatory sequence that is necessary for expression of the nucleotide sequence encoding said oxidoreductase and operably linked to said nucleotide sequence, is foreign to said nucleotide sequence.

13. The expression construct of claim 12, wherein the construct is for expression in a bacterium chosen from the group of *Escherichia, Anabaena, Caulobacter, Gluconobacter, Rhodobacter, Pseudomonas, Paracoccus, Bacillus, Brevibacterium, Corynebacterium, Rhizobium (Sinorhizobium), Flavobacterium, Klebsiella, Enterobacter, Lactobacillus, Lactococcus, Methylobacterium, Staphylococcus* or *Streptomyces* genus; or *B. subtilis, B. amyloliquefaciens, B. lichenifonnis, B. puntis, B. megaterium, B. halodurans, B. pumilus, G. oxydans, Caulobacter crescentus* CB 15, *Methylobacterium extorquens, Rhodobacter sphaeroides, Pseudomonas putida, Paracoccus zeaxanthinifaciens, Paracoccus denitrificans, E. coli, C. glutamicum, Staphylococcus carnosus, Streptomyces lividans, Sinorhizobium melioti* and *Rhizobium radiobacter*species.

14. The expression construct of claim 12, wherein the construct is for expression in yeast cell from the group consisting of the *Candida, Hansenula, Kluyveromyces, Pichia, Saccharomyces, Schizosaccharomyces,* or *Yarrowia* genus; or *Kluyveromyces lactis, S. cerevisiae, Hansenula polymorpha, Yarrowia lipolytica* and *Pichia pastoris* species or in a filamentous fungal cell from the group *Aspergillus, Chrysosporium, Penicillium, Talaromyces* or *Trichoderma* genus; or *Aspergillus niger, Aspergillus awamori, Aspergillus foetidus, Aspergillus sojae, Aspergillus fumigatus, Talaromyces emersonii, Aspergillus oryzae, Chrysosporium lucknowense, Trichoderma reesei* or *Penicillium chrysogenum* species.

* * * * *

SEQUENCE LISTING

<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Synthetic DNA

<400> SEQUENCE: 1
cggaattcca catgacaagg ggagaccg     28

<210> SEQ ID NO 2
<211> LENGTH: 30
<212> TYPE: DNA
<213> ORGANISM: Artificial Sequence
<220> FEATURE:
<223> OTHER INFORMATION: Synthetic DNA

<400> SEQUENCE: 2
cggaattcgc ttcggtcttc aactcggatg     30

<210> SEQ ID NO 3
<211> LENGTH: 579
<212> TYPE: PRT
<213> ORGANISM: Cupriavidus basilensis

<400> SEQUENCE: 3

```
Met Asp Thr Pro Arg Glu Arg Phe Asp Tyr Val Ile Val Gly Gly Gly
 1               5                  10                  15

Ser Ala Gly Cys Val Leu Ala Asn Arg Leu Ser Gln Asp Pro Ala Ile
            20                  25                  30

Arg Val Ala Leu Ile Glu Ala Gly Val Asp Thr Pro Pro Asp Ala Val
        35                  40                  45

Pro Ala Glu Ile Leu Asp Ser Tyr Pro Met Pro Leu Phe Phe Gly Asp
    50                  55                  60

Arg Tyr Ile Trp Pro Ser Leu Gln Ala Arg Ala Val Ala Gly Gly Arg
65                  70                  75                  80

Ser Lys Val Tyr Glu Gln Gly Arg Val Met Gly Gly Ser Ser Ile
                85                  90                  95

Asn Val Gln Ala Ala Asn Arg Gly Leu Pro Arg Asp Tyr Asp Glu Trp
            100                 105                 110

Ala Ala Ser Gly Ala Ser Gly Trp Ser Trp Gln Asp Val Leu Pro Tyr
        115                 120                 125

Phe Arg His Leu Glu Arg Asp Val Asp Tyr Gly Asn Ser Pro Leu His
    130                 135                 140

Gly Ser His Gly Pro Val Pro Ile Arg Arg Ile Leu Pro Gln Ala Trp
145                 150                 155                 160

Pro Pro Phe Cys Thr Glu Phe Ala His Ala Met Gly Arg Ser Gly Leu
                165                 170                 175

Ser Ala Leu Ala Asp Gln Asn Ala Glu Phe Gly Asp Gly Trp Phe Pro
            180                 185                 190

Ala Ala Phe Ser Asn Leu Asp Asp Lys Arg Val Ser Thr Ala Ile Ala
        195                 200                 205

Tyr Leu Asp Ala Asp Thr Arg Arg Ala Asn Leu Arg Ile Tyr Ala
    210                 215                 220

Glu Thr Thr Val Arg Lys Leu Val Ser Gly Arg Glu Ala Arg Gly
225                 230                 235                 240
```

```
Val Ile Ala Met Arg Ala Asp Gly Ser Arg Leu Ala Leu Asp Ala Gly
                245                 250                 255
Glu Val Ile Val Ser Ala Gly Ala Leu Gln Ser Pro Ala Ile Leu Met
            260                 265                 270
Arg Ala Gly Ile Gly Asp Ala Gly Ala Leu Gln Ala Leu Gly Ile Glu
        275                 280                 285
Val Val Ala Asp Arg Pro Gly Val Gly Arg Asn Leu Gln Asp His Pro
    290                 295                 300
Ala Leu Thr Phe Cys Gln Phe Leu Ala Pro Gln Tyr Arg Met Pro Leu
305                 310                 315                 320
Ser Arg Arg Arg Ala Ser Met Thr Ala Ala Arg Phe Ser Ser Gly Val
                325                 330                 335
Pro Gly Gly Glu Ala Ser Asp Met Tyr Leu Ser Ser Thr Arg Ala
            340                 345                 350
Gly Trp His Ala Leu Gly Asn Arg Leu Gly Leu Phe Phe Leu Trp Cys
        355                 360                 365
Asn Arg Pro Phe Ser Arg Gly Gln Val Ser Leu Ala Gly Ala Gln Pro
    370                 375                 380
Asp Val Pro Pro Met Val Glu Leu Asn Leu Leu Asp Asp Glu Arg Asp
385                 390                 395                 400
Leu Arg Arg Met Val Ala Gly Val Arg Lys Leu Val Gln Ile Val Gly
                405                 410                 415
Ala Ser Ala Leu His Gln His Pro Gly Asp Phe Phe Pro Ala Thr Phe
            420                 425                 430
Ser Pro Arg Val Lys Ala Leu Ser Arg Val Ser Arg Gly Asn Val Leu
        435                 440                 445
Leu Thr Glu Leu Leu Gly Ala Val Leu Asp Val Ser Gly Pro Leu Arg
    450                 455                 460
Arg Ser Leu Ile Ala Arg Phe Val Thr Gly Gly Ala Asn Leu Ala Ser
465                 470                 475                 480
Leu Leu Thr Asp Glu Ser Ala Leu Glu Gly Phe Val Arg Gln Ser Val
                485                 490                 495
Phe Gly Val Trp His Ala Ser Gly Thr Cys Arg Met Gly Ala His Ala
            500                 505                 510
Asp Arg Ser Ala Val Thr Asp Ala Ala Gly Arg Val His Asp Val Gly
        515                 520                 525
Arg Leu Arg Val Ile Asp Ala Ser Leu Met Pro Arg Leu Pro Thr Ala
    530                 535                 540
Asn Thr Asn Ile Pro Thr Ile Met Leu Ala Glu Lys Ile Ala Asp Thr
545                 550                 555                 560
Met Gln Ala Glu Arg Arg Ala Val Arg Pro Ala Ser Ser Glu Val Ala
                565                 570                 575
His Pro Ser

<210> SEQ ID NO 4
<211> LENGTH: 1740
<212> TYPE: DNA
<213> ORGANISM: Cupriavidus basilensis

<400> SEQUENCE: 4
atggatacgc cgagggagcg tttcgactac gtgattgttg gcggcgggtc cgccggttgc        60
gtactggcca atcgcctgtc gcaggacccg gccatccgcg tcgcgctgat cgaggcgggc       120
gtcgatacgc cgccggacgc tgtgccggcg gagatcctcg acagctatcc gatgcccttg       180
```

```
ttcttcggtg accggtatat ctggccatcg ctgcaagccc gcgccgtggc aggggcagg    240 tccaaggtct acgagcaagg gcgcgtcatg ggcggcggct ccagcatcaa cgtgcaggcg   300
gcaaaccgcg ggctgccgcg cgactacgat gagtgggccg cgtcgggcgc gtccggatgg   360
tcgtggcagg atgtgctgcc gtatttccgc caccttgagc gcgatgtgga ttacggcaac   420
agcccgctgc acggcagcca cggaccggtg ccgatccgcc gcatcctgcc gcaggcttgg   480
ccgccgttct gcacggagtt tgcgcacgcg atgggccgca gcggcttgtc cgcgctggcc   540
gaccagaacg cggagttcgg cgatggctgg tttccggccg ccttctcgaa cctggatgac   600
aagcgggttt cgaccgccat cgcctatctc gacgcggata cgcgccggcg ggccaatctg   660
cggatctatg ccgagacaac ggtgcgcaag ctcgtcgtat ccggccggga agcgcgtggg   720
gtgatcgcca tgcgggccga tgggtcgcgg ctggcgctgg acgccgggga ggtcatcgtg   780 tccgcggcg ccttgcagtc gcccgccatc ctgatgcgcg cggggatcgg cgacgccggc    840
gcgctgcagg ccctcggcat cgaggtcgta gccgaccgac ccggcgttgg ccgcaatctc   900
caggatcatc ccgcgctgac gttctgccag ttcctcgcgc cccagtaccg catgccgctc   960
tcgcgccggc gcgctagcat gacggcggcg cggttctcat cgggggtgcc aggtggcgag  1020
gcgtcggaca tgtacctgtc cagttccaca cgggcaggct ggcatgcact cggtaatcgg  1080
ctcggcctct tcttcctgtg gtgcaatcgg ccattctcgc gcgggcaggt gagccttgcg  1140
ggagcccagc cggatgtgcc gcccatggtg gagctcaacc tgctcgacga cgagcgggat  1200
ctgcggcgca tggtggccgg cgtacgcaag ttggtgcaga tcgtgggtgc gtcggccttg  1260
catcagcatc ccggtgattt cttccccgct acgttttcgc cgcgcgtcaa ggcgctgagc  1320
cgcgtgagcc gcggcaatgt gttgctcacg gagttgctgg gggcagtgct tgatgtctcg  1380
gggccgctgc gcagaagcct gatcgcgcgc tttgtcacgg gcggcgcaaa cctgccagc   1440 ctgctgacgg atgagtccgc gctagagggc ttcgtgcgcc agagcgtctt cggggtctgg  1500
catgccagcg gcacttgccg gatgggcgcg catgcggacc ggagcgcggt gacggatgcg  1560
gcgggccgcg ttcacgatgt tggcaggctg cgcgttattg acgcctctct gatgccgcgg  1620
ctgccgacgg ccaataccaa catccccacc atcatgctcg cggaaaagat tgccgacacc  1680
atgcaagccg agcgccgcgc ggtccggccg gcatcgagcg aagttgccca tccgagttga  1740
```